United States Patent [19]

Kettner

[11] Patent Number: 5,384,410
[45] Date of Patent: Jan. 24, 1995

[54] REMOVAL OF BORONIC ACID PROTECTING GROUPS BY TRANSESTERIFICATION

[75] Inventor: Charles A. Kettner, Wilmington, Del.

[73] Assignee: The Du Pont Merck Pharmaceutical Company, Wilmington, Del.

[21] Appl. No.: 36,378

[22] Filed: Mar. 24, 1993

[51] Int. Cl.⁶ .............. C07D 207/14; C07F 5/02; C07F 5/04

[52] U.S. Cl. .............. 548/405; 530/326; 530/327; 530/328; 530/329; 530/330; 530/331; 558/288; 558/289; 558/295; 558/298; 558/384; 562/7

[58] Field of Search .............. 562/7; 558/228, 289, 558/295, 298, 384; 548/405; 530/331, 330

[56] References Cited

U.S. PATENT DOCUMENTS 4,499,082  2/1985  Shenvi et al. .............. 514/2
4,537,773  8/1985  Shenvi .............. 514/63

FOREIGN PATENT DOCUMENTS

0293881A2  12/1988  European Pat. Off. .

OTHER PUBLICATIONS

Gross & Meienhofer; "The Peptides, Analysis, Synthesis, Biology"; vol. 3, (1981), pp. 1 to 98 and 341 to 448; Academic Press, N.Y.

Kettner and Shenvi, The Journal of Biological Chemistry 259; pp. 15106–15112, (1984).

Matteson, Chemistry Review 89; (1989), pp. 1535–1551.

*Primary Examiner*—Joseph Paul Brust
*Attorney, Agent, or Firm*—Norbert F. Reinert

[57] ABSTRACT

A method for the removal of ester protecting groups from α-amino boronic acid is disclosed for the preparation of compounds of formula (II) below $$R^1-X_n-NHCH(R^2)-B(OH)_2$$

8 Claims, No Drawings

REMOVAL OF BORONIC ACID PROTECTING GROUPS BY TRANSESTERIFICATION

FIELD OF THE INVENTION

The present invention relates to a process for the removal of ester protecting groups from α-amino boronic acids and corresponding peptide analogs by transesterification with hydrophobic boronic acids.

BACKGROUND OF THE INVENTION

Simple boronic acids are inhibitors of serine proteases. For example, Koehler et al. *Biochemistry* 10: 2477 (1971) reports that 2-phenylethane boronic acid inhibits chymotrypsin at millimolar levels. The synthesis of boronic acid analogs of N-acyl-a-amino acids has yielded more effective inhibitors. Ac-boroPhe-OH, R-1-acetamido-2-phenylethane boronic acid, inhibits chymotrypsin with a $K_i$ of 4 μM Matteson et al. *J. Am. Chem. Soc.* 103: 5241 (1981). More recently, Shenvi, U.S. Pat No. 4,537,773 (1985) disclosed that boronic acid analogs of α-amino acids, containing a free amino group, were effective inhibitors of aminopeptidases. Shenvi, U.S. Pat. No. 4,499,082 (1985) discloses that peptides containing an α-amino boronic acid with a neutral side chain were more effective inhibitors of serine proteases exceeding inhibitors disclosed earlier by as much as 3 orders of magnitude in potency. The chemistry of α-aminoboronic acids was further expanded to the synthesis of peptide analogs containing boronic acid with positive charged side chains, boroLysine, boroArginine, boroOrnithine, and isothiouronium analogs. This is disclosed in Kettner, et al. EPA 0,293,881, published Dec. 7, 1988.

Much progress has been made in the synthesis of boronic acid and corresponding peptides with the boronic acid protected as an ester. However, a convenient method of removal of the ester protecting group is lacking. Matteson (1981) infra, reports the destructive removal of pinanediol group by treatment with anhydrous $BCl_3$. Kettner and Shenvi *J. Biol. Chem.* 259: 15106 (1984) describe the removal of the pinacol protecting group by converting the boronic pinacol esters to the thermodynamically more stable, diethanolamine ester by transesterification and then hydrolysis by treatment with aqueous acid or with a cation exchange resin. This method is not applicable for removal of pinanediol ester due to its greater stability. Matteson *Chem. Rev.* 89: 1535 (1989) describes the removal of the pinanediol group in situ by incubations in borate buffer. It should be noted that the pinanediol ester is preferred in synthesis due to it ability to direct stereochemistry at the α-carbon of boronic acid and its stability to chemical manipulations. The pinanediol protecting group was used almost exclusively in the preparation of boroArginine peptides, shown in EPA 0,293,881. In one example, partial hydrolysis of the pinanediol ester was obtained by binding Ac-(D)Phe-Pro-boroArg-$C_{10}H_{16}$ to a cation exchange resin and washing extensively with aqueous acetic acid followed by elution with HCl. This reaction is slow, it requires recovery of product by evaporation of large volumes of water and separation of the free boronic acid from the ester. Removal of the pinanediol by treatment with $BCl_3$ as the final step in synthesis was considered to be the only practical method.

SUMMARY OF THE INVENTION

The present invention provides a method for converting compounds of formula I $$R^1\text{-}X_n\text{-NHCH}(R^2)\text{-}BR^3R^4 \quad (I)$$

to compounds of formula II, $$R^1\text{-}X_n\text{-NHCH}(R^2)\text{-}B(OH)_2 \quad (II)$$

wherein for both formula I and formula II
$R^1$ is
  a) hydrogen,
  b) an N-terminal protecting group,
  c) $-SO_2(CH_2)_m$-aryl, wherein aryl is phenyl, napthyl or biphenyl substituted with one, two or three substituents selected from the group consisting of halo (F, Cl, Br, I,), $-CN$, C1-C10-alkyl, C3-C8-cycloalkyl, C2-C10-alkenyl, C2-C10-alkynyl, $-OR^7$, $-NO_2$, $-CF_3$, $-S(O)_rR^8$, $-NR^6R^7$, $-COR^7$, $-CO_2R^7$, $-CONR^6R^7$;
X is a peptide of 1–20 amino acids;
$R^2$ is
  a) C1-C10-alkyl,
  b) C2-C10-alkyl-Y,
  c) $-(CH_2)_n$-aryl, wherein aryl is as defined above;
Y is
  a) $-NHC(NH)NH_2$,
  b) $-NH_2$,
  c) $-SC(NH)NH_2$,
  d) $-OR^9$,
  e) $-SR^9$;
$R^3$ and $R^4$ are
  a) C1-C8-alkoxy, or
  b) when taken together $R^3$ and $R^4$ form a cyclic boronic ester where said chain or ring contains from 2 to 20 carbon atoms and, optionally, a heteroatom which can be N, S, or O;
$R^5$ and $R^6$ are independently
  a) H,
  b) C1-C8-alkyl,
  c) C1-C8-alkoxy,
  d) C3-C8-cycloalkyl,
  e) $-CO_2R^7$,
  f) $-(CH_2)_m$-phenyl;
$R^7$ is
  a) H,
  b) phenyl,
  c) benzyl,
  d) C1-C8-alkyl;
$R^8$ is
  a) phenyl,
  b) C1-C4-alkyl,
  c) C1-C4-alkoxy,
  d) $-CF_3$;
$R^9$ is
  a) H,
  b) C1-C2-alkyl,
  c) phenyl or phenyl optionally substituted with a substituent selected from the group consisting of halo (F, Cl, Br, I), $-CN$; C1-C10-alkyl, C3-C8-cycloalkyl, C2-C10-alkenyl, $-C2-C10$-alkynyl, $-OR^7$, $-NO_2$, $-CF_3$, $-S(O)_rR^8$, $-NR^6R^7$, $-COR^7$, $-CO_2R^7$, $-CONR^6R^7$ wherein $R^5$, $R^6$, and $R^8$ are as defined above;
n is 0 or 1;
m is 0 to 2;

r is 0 to 2;
which comprises reacting a compound represented by formula I in a mixture of water and a water-immiscible organic solvent containing an organic boronic acid acceptor present in an amount equal to at least 1 equivalent of the compound of formula I, stirring the mixture at a temperature in a range of from about 5° to about 35° C. for a time of approximately 1 hour, allowing the mixture to then separate into two distinct phases, separating the phases and then recovering the desired compound of formula II from the separated aqueous phase.

DETAILED DESCRIPTION OF THE INVENTION

As used throughout the specifications, the following abbreviations for amino acid residues or amino acids apply:
Ala=L-alanine
Arg=L-arginine
Asn=L-asparagine
Asp=L-aspartic acid
Cys=L-cysteine
Gln=L-glutamine
Glu=L-glutamic acid
Gly=glycine
His=L-histidine
Ile=L-isoleucine
Leu=L-leucine
Lys=L-lysine
Met=L-methionine
Phe=L-phenlyalanine
Pro=L-proline
Ser=L-serine
Thr=L-threonine
Trp=L-tryptophan
Tyr=L-tyrosine
Val=L-valine The "D" prefix for the foregoing abbreviations indicates the amino acid is in the D-configuration. "D,L" indicates the amino is present in mixture of the D- and the L-configurations.

Other abbreviations used throughout the description below are:
Me=methyl
Et=ethyl
Boc=t-butoxycarbonyl
Z=benzyloxycarbonyl
2Clz=2-chlorobenzyloxycarbonyl
4Clz=4-chlorobenzyloxycarbonyl
p-NO$_2$-Z=p-NO$_2$benzyloxycarbonyl
AC=acetyl
Adc=adamantyloxycarbonyl
DIPA=diisopropylamine
DIPEA=diisopropylethylamine
DCHA=dicyclohexylamine
DBU=1,8-diazabicyclo[5.4.0]undec-7-ene
DABCO=1,4-diazabicyclo[2.2.2]octane
NMM=N-methylmorpholine
DMAP=4-dimethylaminopyridine
FSA=formamidinesulfinic acid
FAB/MS=fast atom bombardment mass spectrometry
MS(NH$_3$-Cl)=chemical ionization mass spectrometry
NMR=nuclear magnetic resonance spectrometry The following reagents were obtained from commercial sources: 1-hydroxybenzotriazole.H$_2$O, adamantylfluoroformate, di-t-butyldicarbonate, benzyloxycarbonyl chloride, 2-chlorobenzyloxycarbonyl chloride, N-hydroxysuccinimide, formamidinesulfinic acid, 32% peracetic acid.

Boc-Pro-boroOrn-C$_{10}$H$_{16}$, Ac-(D)Phe-Pro-boroOrn-C$_{10}$H$_{16}$, BocPhe-boroOrn-C$_{10}$H$_{16}$ benzenesulfonic acid were prepared by the procedure described in EP02938-81A2, p12-13.

The prefix "boro" indicates amino acid residues where the carboxy group is replaced by a boronic acid (formula II, R$^3$ and R$^4$=—OH).

The pinanediol boronic acid ester and the pinacol boronic acid ester are abbreviated "—C$_{10}$H$_{16}$" and "C$_6$H$_{12}$", respectively. Other illustrations of diols useful for deriving a boronic acid esters are 1,2-ethanediol, 1,3-propanediol, 2,3-butanediol, 1,2-diisopropylethanediol, 5,6-decanediol, 1,2dicyclohexylethanediol.

Note that throughout the text when an alkyl substituent is mentioned, the normal alkyl structure is meant (e.g. butyl is n-butyl) unless otherwise specified. However, in the definition of radicals above (e.g. R$^2$), both branched and straight chains are included in the scope of alkyl.

It is understood that many of the compounds of the present invention contain one or more chiral centers and that these stereoisomers may possess distinct physical and biological properties. The present invention comprises all of the stereoisomers or mixtures thereof. If the pure enantiomers or diastereomers are desired, they may be prepared using starting 15 materials with the appropriate stereochemistry, or may be separated from mixtures of undesired stereoisomers by standard techniques, including chiral chromatography and recrystallization of diastereomeric salts.

"N-terminal protecting group" as used herein, refers to various art recognized amino-terminal protecting groups employed in peptide synthesis. Examples of suitable groups include formyl, acetyl, benzoyl, trifluoroacetyl, and methoxysuccinyl; aromatic urethane protecting groups, such as, benzyloxycarbonyl; and aliphatic urethane protecting groups, such as t-benzyloxycarbonyl or adamantyloxycarbonyl. Gross and Meinhoffer, eds., The Peptides, Vol. 3; 3-88 (1981), Academic Press, New York 1981, disclose numerous suitable amine protecting groups and is incorporated herein by reference for that purpose.

"Peptide of 1-20 amino acids" as used herein, refers to a peptide chain of one to twenty natural or unnatural amino acids of either D- or L-configuration. Roberts and Vellaccio, The Peptides, Vol. 5; 341-449, Academic Press, New York 1983, disclose numerous suitable natural and unatural amino acids and is incorporated herein by reference for that purpose. This term is also intended to include sidechain protected amino acid residues that are commonly employed in peptide synthesis such as those disclosed in the Peptides, Vol 3, 3-88 (1981). This reference is incorporated herein by reference for that purpose.

It should be noted that to yield a compound of formula II where X is a peptide, optionally, the N-terminal or sidechain protecting groups can be removed by using procedures well known to those skilled in the art. For example, where the N-terminal or side chain protecting group is BOC, the BOC group can be removed by treatment with Anhydrous HCL. Where the N-terminal or side chain protecting group is Z, the Z group can be removed by means of catalytic hydrogenation.

The present invention relates to the synthesis of free boronic acids (compounds of formula II) from ester precursors by transesterification reactions with aliphatic and aromatic boronic acids under heterogeneous reaction conditions.

Scheme 1

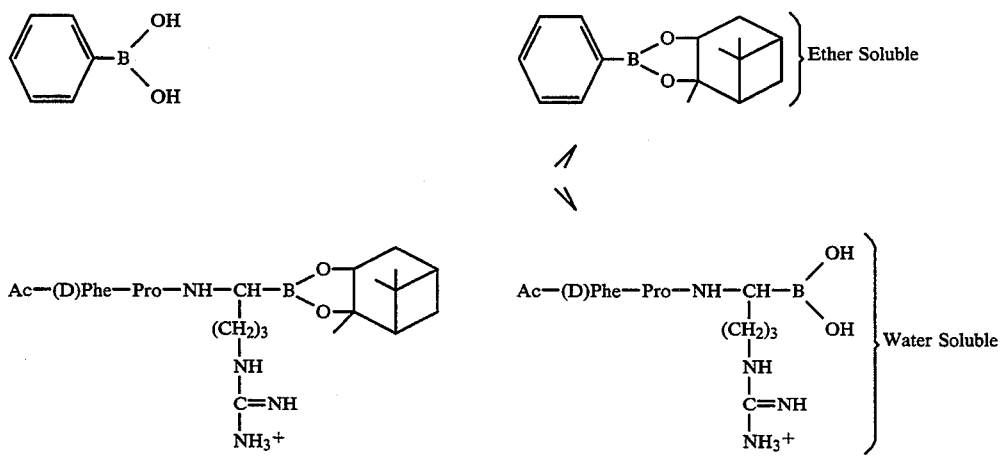

This novel method is readily applicable to compounds where the $R^2$ side chain is positively charged as shown in Scheme 1 where $R^2$ is the 3-guanidino-propyl moiety. In this example, the protected boronic acid ester, Ac-(D)Phe-Pro-boroArg-$C_{10}H_{16}$, is suspended in a mixture consisting of water, an equal volume of diethyl ether, and 5 equivalents of phenyl boronic acid. The flask is stoppered and allowed to stir rapidly with a magnetic stirrer at room temperature. Two clear phases are observed after 15–30 min. Stirring is continued for 3 hr. The reaction mixture is transferred to a separatory funnel where the phases are separated. The aqueous phase is then washed with two portions of ether. Water is removed by evaporation at 35°–43° C. at a reduced pressure. Products are usually obtained as white foams after drying in vacuo. with KOH and $P_2O_5$ and are readily converted to amorphous white solids by triturating with ether.

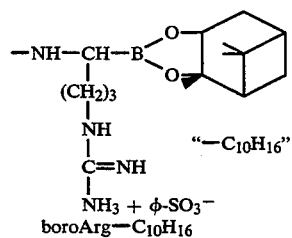

boroArg—$C_{10}H_{16}$

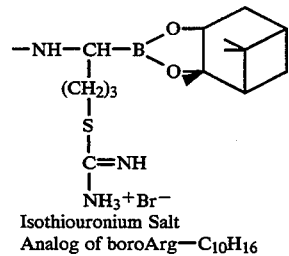

Isothiouronium Salt
Analog of boroArg—$C_{10}H_{16}$

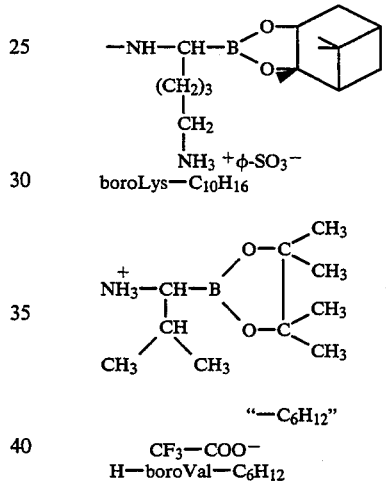

boroLys—$C_{10}H_{16}$

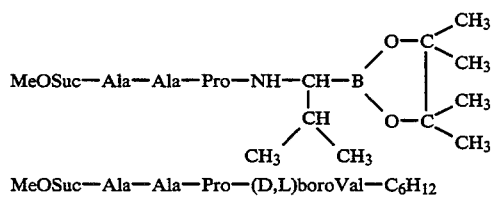

"—$C_6H_{12}$"

$CF_3$—$COO^-$
H—boroVal—$C_6H_{12}$

MeOSuc—Ala—Ala—Pro—NH—CH—B(...)
MeOSuc—Ala—Ala—Pro—(D,L)boroVal—$C_6H_{12}$

The above process depends on the final product being more soluble in the aqueous phase than the organic phase. This criteria is readily met for compounds such as the boroArginine, boroLysine, and boroOrnithine peptides as well as analogs were the isothiouronium group replaces the guanidino group. It is applicable to compounds in U.S. Pat. Nos. 4,537,773 and 4,499,082 which describe α-aminoboronic acids with neutral side chains and peptides containing α-aminoboronic acids with neutral side chains, respectively. For removal of the ester protecting group from α-aminoboronic such as H-boroVal-$C_6H_{12}$, this method should be generally applicable since these compounds are readily soluble in water due to the presence of the free α-amino group. It should be applicable to a large number of less hydrophobic peptide boronic acids which are readily soluble in water. For example, the pinacol protecting group of MeOSuc-Ala-Ala-Pro-boroVal-OH is readily removed by the method of the present invention. However, it will be desirable to run trial reactions on a small scale to determine the solubility of the free boronic acid product and the feasibility of this method. For more hydrophobic compounds in this series, it maybe necessary to design a synthetic protocol were the transesterification step is applied to intermediates containing charged residues.

The use of a biphasic system with the organic phase consisting of diethyl ether and phenyl boronic appears to be ideal for the preparation of most free boronic acids. This method will be applicable to the removal of other boronic acid protecting groups represented by $R^3$ and $R^4$ in formula (I). Specific examples, in addition to the pinanediol and pinacol groups, are where $R^3$ and $R^4$ taken together form a moiety derived from 1,2-ethanediol, 1,3-propanediol, 2,3butanediol, 1,2-diisopropylethanediol, 5,6-decanediol, or 1,2-dicyclohexylethanediol. The protecting groups can also be where $R^3$ and $R^4$ are derived from alcohols such as isopropanol, methanol, ethanol or n-propanol. Of course, $R^3$ and $R^4$ can each be derived from the same alcohol or from different alcohols, if desired.

Organic solvents other than diethyl ether can be used in the method of the invention. It is only necessary that the organic solvent be water immiscible. Suitable choices of other organic solvents are carbonteterachloride, chloroform, methylenechloride, ethyl acetate, benzene, tolulene or hexane.

Boronic acid acceptors for the ester protecting group other than phenyl boronic acid also can be used in the method of the invention. It is only necessary that the acceptor boronic acid, both in its free form and in its esterified form, have greater solubility in the organic phase than in the aqueous phase. Suitable choices of other acceptor boronic acids are butyl boronic acid, pentyl boronic acid, hexyl boronic acid or cyclohexyl boronic acid.

For the method of invention, the ratio of water to organic solvent in the mixture in which the ester precursor of formula (I) is suspended can vary widely. It is important that sufficient volumes of water and organic solvent be present to completely dissolve the products of the reaction (acceptor boronic acid plus ester for the organic phase and free boronic acid for the aqueous phase).

For the method of the invention, the amount of acceptor boronic acid in the reaction mixture should be an amount equal to at least a molar equivalent of the ester precursor of formula (I) present in said mixture. Generally, it is preferable to have the acceptor boronic acid present in an amount in excess of an equimolar amount, the most preferred amount being a range of from 3 to 5 equivalents.

The time of stirring the reaction mixture can vary over wide limits depending on the ester precursor and the acceptor boronic acid involved. Usually, the minimum time for stirring is 1 hour, but can vary from 0.2 to 48 hours.

In the method of the invention, the desired product compound of formula (II) is recovered from the aqueous phase after its separation from the two phase system formed from stirring the reaction mixture. This is best accomplished by the removal of water from the aqueous phase by means well understood by those skilled in the art, such as with a rotary evaporator.

NMR, proton nuclear magnetic resonance, chemical shifts are reported in $\delta$ units, parts per million downfield from the internal tetramethylsilane standard. Elemental analyses were conducted by Galbraith Laboratories Inc., Knoxville, Tenn. and Microanalysis Inc., Wilmington, Del. FAB/MS samples of free boronic acids did not give consistent results making it difficult to monitor the removal of ester protecting groups difficult by this means. However, the presence of the pinanediol and the pinacol groups are readily observed in NMR spectra. For the pinanediol ester, a methyl group is observed at $\delta$0.9 and the methyl groups of the pinacol groups are observed as singlet at $\delta$1.1 Following the removal of pinanediol protecting group, FAB/MS were run by treating the sample with ~2 equivalents of pinacol in methanol for 5 min and evaporating the solvent. Similarly, FAB/MS samples of free boronic acid, obtained by removal of the pinacol, were prepared by treating with pinanediol.

EXAMPLE 1

Preparation of Ac-(D)Phe-Pro-boroArg-OH.benzene, sulfonic acid

The synthesis of Ac-(D)Phe-Pro-boroArg$C_{10}H_{16}$.benzene sulfonic acid has been described previously, Kettner et al. *J. Biol Chem* 265: 18289 (1990).

Ac-(D)Phe-Pro-boroArg-$C_{10}H_{16}$.benzene sulfonic acid (0.20 g, 0.27 moles) and phenyl boronic acid (0.16 g, 1.3 moles) were suspended in a mixture consisting of 5 ml of water and 5 ml of ether. The mixture was stirred overnight at room temperature. The two phases were separated, the organic phase was washed with water, and the aqueous phase was washed with ether. The combined aqueous phases was evaporated to yield 0.14 g of product. NMR was consistent with the desired structure and the product obtained in Example 2.

EXAMPLE 2

Preparation of Ac-(D)Phe-Pro-boroArg-OH.HCl

Ac-(D)Phe-Pro-boroArg-$C_{10}H_{16}$.benzene sulfonic acid (6.4 g, 8.5 mmoles) and phenyl boronic acid (5.2 g, 42 moles) were suspended in 150 ml of water and 150 ml of ether. The mixture was stirred overnight. The phases were separated and the ether phase was washed with two 100 ml portions of water. The combined aqueous phases were washed with ether. The aqueous phase was concentrated to ~50 ml by evaporation and then it was passed through a column containing 15 ml of Bi-oRad ™ AG1-X8 (Cl⁻ form). The aqueous phase was further concentrated to ~2 ml and it was chromatogramed on a 2.5×100 cm column containing Bi-oRad ™ P₂ resin and equilbrated with 1.0 mM HCl. Fractions containing the desired product were pooled, evaporated, dried in vacuo. and triturated with ether to yield 3.4 g.

Anal. Calcd. for $C_{21}H_{34}N_6O_5BCl$: C=50.77%, H=6.91%, N=16.92%, and B=2.18%. Found: C=50.91%, H=6.97%, N=16.91%, B=2.29%.

EXAMPLE 3

Preparation of Ac-Phe-Pro-boroArg-OH.HCl

The starting material for this reaction, Ac-Phe-Pro-boroArg-$C_{10}H_{16}$.HCl, was prepared by coupling Ac-Phe-OH to H-Pro-boroArg-$C_{10}H_{16}$. The intermediate Boc-Pro-boroOrn-$C_{10}H_{16}$ was prepared by the procedure described in EPA 0 293 881 and it was guanidated using aminoiminomethane sulfonic acid [Mosher et al. *Tetrahedral Lett.* 29: 3183 (1988)]. Boc-Pro-boroOrnC- $_{10}H_{16}$-benzene sulfonic acid (4.8 g, 10.4 mmoles) was dissolved in 50 ml of absolute ethanol; 4-dimethylaminopyridine (2.5 g, 20.7 mmoles) and aminoiminomethane sulfonic acid (2.6 g, 20.7 mmoles) were added. The mixture was refluxed at 80° C. for 3 hrs. It was cooled and solids were removed by filtration. Solvent was evaporated, the residue was dissolved in chloroform, and it was washed with 0.2 N HCl prepared in saturated aqueous NaCl and with saturated aqueous NaCl. After drying over anhydrous sodium sulfate, solvent was evaporated to yield 5.4 g of a foam. This material was dissolved in methanol and it was chromatogramed on a 2.5×100 cm column of Sephadex ™ LH-20 using methanol as a solvent. Product, 4.4 g, was obtained. FAB/MS calcd. for M ($C_{25}H_{44}N_5O_5B$)+H: 506.56. Found: 506.49.

H-Pro-boroArg-$C_{10}H_{16}$.2HCl was prepared by dissolving Boc-Pro-boroArg-$C_{10}H_{16}$.HCl (1.3 g, 2.4 mmoles) in 10 ml of dioxane and adding 10 ml of 3.3N HCl: dioxane. After stirring for 2 hrs, solvent was evaporated and the residue was triturated with ether to yield 1.2 g of product. FAB/MS calcd. for M ($C_{20}H_{36}N_5O_3B$) +H: 406.43. Found: 406.38.

Ac-Phe-OH (87 mg, 0.42 mmoles) was coupled to H-Pro-boroArg-$C_{10}H_{16}$.2HCl (200 mg, 0.42 mmoles) using the carbodiimide procedure. The starting materials were dissolved in 20 ml of methylene chloride, N-methylmorpholine (92 µl, 0.84 mmoles), 1-hydroxybenzotriazole.$H_2O$ (130 mg, 0.84 mmoles), and dicyclohexylcarbodiimide (86 mg, 0.42 mmoles) were added. After stirring overnight at room temperature, the reaction mixture was filtered, the filtrate evaporated, and the residue was chromatogramed 2.5×50 cm column of LH-20 using methanol as a solvent. The desired product was obtained in a yield of 240 mg. FAB/MS calcd. for M ($C_{31}H_{47}N_6O_5B$)+H: 595.66. Found: 95.41.

Ac-Phe-Pro-boroArg-$C_{10}H_{16}$.HCl (0.13 g, 0.21 mmoles) and phenyl boronic acid (0.13 g, 1.0 mmoles) were dissolved in a mixture of 5 ml of water and 5 ml of ether. The mixture was stirred 3 hrs at room temperature. The reaction phases were separated and the aqueous phase was extensively washed with ether. Water was evaporated and the residue dried to yield 0.11 g. The product was triturated with ether to yield a white solid. FAB/MS calcd. for the pinacol ester, M ($C_{27}H_{43}N_6O_5B$)+H: 543.58. Found: 543.48.

EXAMPLE 4

Preparation of Ac-Pro-boroArg-OH.HCl

Ac-Pro-boroArg-$C_{10}H_{16}$.HCl was prepared by dissolving H-Pro-boroArg-$C_{10}H_{16}$.2HCl (200 mg, 0.41 mmoles) in 1 ml of dioxane: water (1:1) and adding acetic anhydride (59 µl, 0.63 mmoles) and sodium bicarbonate (110 mg, 1.2 mmoles). The reaction was allowed to stir 30 min at room temperature, it was acidified with HCl, diluted with methanol, and evaporated. It was redissolved in methanol and chromatogramed on 2.5×50 cm column of LH-20. Fractions containing the desired product were pooled, evaporated, and triturated with ether to yield 140 mg. FAB/MS calcd. for M ($C_{22}H_{38}N_5O_4B$)+H: 447.97. Found: 448.43.

The conditions in Example 3 were used to prepare the free boronic acid of Ac-Pro-boroArg-$C_{10}H_{16}$.HCl (0.12 g, 0.24 mmoles). After triturating the product with ether, 0.080 g of Ac-Pro-boroArg-OH.HCl were obtained. FAB/MS calcd. for the pinacol ester, M ($C_{18}H_{34}N_5O_4B$)+H: 396.39. Found: 396.3.

EXAMPLE 5

Preparation of Ac-Gly-boroArg-OH.benzene sulfonic acid

Boc-Gly-boroArg-$C_{10}H_{16}$ (10.2 g) was prepared from Boc-Gly-boroOrn-$C_{10}H_{16}$.benzene sulfonic acid (12.5 g, 21.5 mmoles) by the procedure described in EPA 0 293 881. FAB/MS calcd. for M ($C_{22}H_{40}N_5O_5B$)+H: 466.32. Found: 466.59.

H-Gly-boroArg-$C_{10}H_{16}$.HCl, benzene sulfonic acid was prepared by deblocking Boc-Gly-boroArg-$C_{10}H_{16}$ with HCl: dioxane.

Ac-Gly-boroArg-$C_{10}H_{16}$.benzene sulfonic acid was prepared by the procedure described for Ac-Pro-boroArg-$C_{10}H_{16}$ in Example 4. FAB/MS calcd. for M ($C_{19}H_{34}N_5O_4B$)+H: 407.90. Found: 408.36.

The condition described for Example 3 were used to prepare the free boronic acid. Ac-Gly-boroArg-$C_{10}H_{16}$.benzene sulfonic acid (0.064 g, 0.11 mmoles) yielded 33 mg of Ac-Gly-boroArg-OH.benzene sulfonic acid. FAB/MS calcd. for the pinacol ester, M ($C_{15}H_{30}N_5O_4B$)+H: 356.32. Found: 356.3.

EXAMPLE 6

Preparation of Ac-(D)Phe-Gly-boroArg-OH.benzene sulfonic acid

Ac-(D)Phe-Gly-boroArg-$C_{10}H_{16}$.benzene sulfonic acid was prepared by coupling Ac-(D)Phe-OH to H-Gly-boroArg-$C_{10}H_{16}$ using a modification of the carbodiimide procedure described in Example 3. For this coupling, 2 ml of dimethylformamide was used with 20 ml of methylene chloride as a solvent. FAB/MS calcd. for M ($C_{28}H_{43}N_6O_5B$)+H: 555.59. Found: 555.38.

The procedure described in Example 3 was used to prepare the free boronic acid. Ac-(D)Phe-Gly-boroArg-$C_{10}H_{16}$.benzene sulfonic acid (0.10 g, 0.14 mmoles) yielded 72 mg of Ac-(D)Phe-Gly-boroArg-OH.benzene sulfonic acid. FAB/MS calcd. for the pinacol ester M ($C_{24}H_{39}N_6O_5B$)+H: 503.51. Found: 503.32.

EXAMPLE 7

Preparation of Boc-(D)Phe-Gly-boroArg-OH.HCl

Boc-(D)Phe-Gly-boroArg-$C_{10}H_{16}$ was prepared by coupling Boc-(D)Phe-OH to the dipeptide analog using the mixed anhydride procedure. The mixed anhydride of Boc-(D)Phe-OH (95 mg, 0.36 mmoles) was prepared by dissolving the acid in 3 ml of anhydrous tetrahydrofuran and adding N-methylmorpholine (40 µl, 0.36 mmoles), and isobutyl chloroformate (46 µl, 0.36 mmoles) at −20° C. After 5 min, triethylamine (50 µl, 0.36 mmoles) and 10 ml of cold tetrahydofuran were added and the mixture was immediately added to a 0° C. solution of H-Gly-boroArg-$C_{10}H_{16}$.benzene sulfonic acid, HCl (200 mg, 0.36 mmoles) in 6 ml of chloroform. After allowing the reaction to warm to room temperature and to stir several hrs, it was filtered and solvent was evaporated. The residue was chromatogramed on a 2.5×50 cm column of LH-20 in methanol to yield 210 mg of the desired product. FAB/MS calcd. for M ($C_{31}H_{49}N_6O_6B$)+H: 613.39. Found: 613.65.

The procedure described in Example 3 was used to convert Boc-(D)Phe-Gly-boroArg-$C_{10}H_{16}$.HCl (0.050 g, 0.077 moles) to 36 mg of Boc-(D)Phe-Gly-boroArg-OH.HCl. FAB/MS calcd. for the pinacol ester, M ($C_{27}H_{45}N_6O_6B$)+H: 561.60. Found: 561.4.

EXAMPLE 8

Preparation of Ac-Phe-Gly-boroArg-OH.benzene sulfonic acid

Ac-phe-Gly-boroArg-$C_{10}H_{16}$.benzene sulfonic acid was prepared by coupling Ac-Phe-OH to H-Gly-boroArg-$C_{10}H_{16}$ using the carbodiimide procedure described in Example 3. FAB/MS calcd for M ($C_{24}H_{39}N_6O_5B$). 503.51. Found: 503.3.

Ac-phe-Gly-boroArg-$C_{10}H_{16}$.benzene sulfonic acid (0.075 g, 0.10 mmoles) was treated with phenyl boronic acid by the procedure in Example 3 to yield Ac-Phe-Gly-boroArg-OH.benzene sulfonic acid. FAB/MS calcd. for the pinacol ester, M ($C_{27}H_{43}N_4O_5B$)+H: 515.48. Found: 515.3.

EXAMPLE 9

Preparation of Ac-(D)Phe-Pro-boroLys-OH.benzene sulfonic acid

The intermediate, $NH_2$—$CH[(CH_2)_4Br]BO2C_{10}H_{16}$.HCl was prepared by the procedure described for the analogous compound, $NH_2$—$CH[(CH_2)_3Br]BO_2C_{10}H_{16}$.HCl, in EPA 0 293 88Q. Also by analogous reactions, Ac-(D)Phe-Pro-NH—$CH[(CH_2)_4Br]BO_2C_{10}H_{16}$, Ac-(D)Phe-Pro-NH—$CH[(CH_2)_4N_3]BO_2C_{10}H_{16}$, and Ac-(D)Phe-Pro-NH—$CH[(CH_2)_4NH_2]BO_2C_{10}H_{16}$.benzene sulfonic acid (Ac-(D)Phe-Pro-boroLys-$C_{10}H_{16}$.benzene sulfonic acid) were prepared.

Ac-(D) Phe-Pro-boroLys-$C_{10}H_{16}$.benzene sulfonic acid (0.50 g, 0.76 mmoles) was treated with phenyl boronic acid by the procedure described in Example 3 to yield Ac-(D)Phe-Pro-boroLys-OH.benzene sulfonic acid (0.35 g). FAB/MS calcd. for the pinacol ester, M ($C_{27}H_{43}N_4O_5B$)+H: 515.48. Found: 515.3.

EXAMPLE 10

Preparation of the Isothiouronium Analog of Ac-(D)Phe-Pro-boroArg-OH

Ac-(D)Phe-Pro-NH—$CH[(CH_2)_3$-S-C(NH)-$NH_2]BO_2$-$C_{10}H_{16}$.HBr. was prepared by the procedure described in EPA 0 293 881. The corresponding bromide was treated with thiourea to yield the desired produce as an amorphous white solid. Anal. Calcd. for $C_{31}H_{47}N_5SBBr$: C=53.75%, H=6.85%, N=10.11%, B=1.56%. Found: C=53.18%, H=6.68%, N=9.47%, and B=1.50%. FAB/MS calcd. for the pinacol ester, M ($C_{31}H_{46}N_5SB$)+H: 612.71. Found: 612.36.

Ac-(D)Phe-Pro-NH—$CH[(CH_2)_3$-S-C(NH)-$NH_2]BO_2$-$C_{10}H_{16}$.HBr (1.0 g, 1.4 mmoles) was allowed to react with phenyl boronic acid by the procedure in Example 3 to yield 0.66 g of the desired product, Ac-(D)Phe-Pro-NH—$CH[(CH_2)_3$-S-C(NH)-$NH_2]B(OH)_2$.HBr. Anal. Calcd. for $C_{21}H_{33}N_5O_5SBBr$: C=45.17%, H=5.97%, N=12.55%, and B=1.93%. Found: C=44.78%, H=5.58%, N=12.23%, and B=1.85%. FAB/MS calcd. for the pinacol ester, M ($C_{27}H_{42}N_5O_5BS$)+H: 560.31. Found: 560.41.

EXAMPLE 11

Preparation of MeOSuc-Ala-Ala-Pro-(D,L)boroVal-OH

The synthesis of MeOSuc-Ala-Ala-Pro-(D,L)boroVal-$C_6H_{12}$ has been described previously, Kettner and Shenvi *J. Biol. Chem.* 259: 15106 (1984). The pinacol ester (100 mg, 0.17 mmoles) was allowed to react with 5 equivalent of phenyl boronic acid using the conditions described in Example 3. The aqueous phase was evaporated to yield 92 mg of MeOSuc-Ala-Ala-Pro-(D,L)boroVal-OH. NMR indicated only a trace (<10%) of the pinacol group remained. FAB/MS calcd. for the pinanediol ester, M ($C_{30}H_{49}N_4O_8B$)+H: 605.65. Found: 605.4.

EXAMPLE 12

Preparation of H-(D,L)boroVal-OH

H-(D,L)boroVal-$C_6H_{12}$.trifluoroacetic acid (100 mg, 0.32 mmoles), described in Kettner and Shenvi (1984) was allowed to react with phenyl boronic acid by the procedure in Example 3. H-(D,L)boroVal-OH.trifluoroacetic acid was obtained in a yield of 76 mg. NMR was consistent with the desired structure indicating the complete absence of the pinacol group. FAB/MS calcd. for the pinanediol ester, M ($C_{14}H_{26}NO_2B$)+H: 252.22. Found: 252.2.

EXAMPLE 13

Preparation of hydrocinnamoyl-Pro-boroLys-OH benzene sulfonic acid.

Hydrocinnamoyl-Pro-boroLys-$C_{10}H_{16}$ benzene sulfonic acid was prepared by the general procedure described in EPA 0 293 881 and was allowed to react with phenyl boronic acid by the procedure in Example 3. The desired product was obtained in a yield of 92%. MS calcd. for M($C_{19}H_{30}N_3O_4B$)+H-$2H_2O$: 340.0 Found: 340. Anal Calcd. for $C_{35}H_{50}N_3O_7SB$: c=62.96%, H=7.55%, N=6.29%, B=1.62%. Found: C=62.75%, H=7.47%, N=6.28%, B=1.64%.

What is claimed is:

1. A method for the preparation of a compound of formula (II)

$$R^1\text{-}X_n\text{—}NHCH(R^2)\text{-}B(OH)_2 \qquad (II)$$

wherein $R^1$ is a) hydrogen, b) an N-terminal protecting group, c) —$SO_2(CH_2)_m$-aryl, wherein aryl is phenyl, napthyl or biphenyl substituted with one, two or three substituents selected from the group consisting of halo (F, Cl, Br, I,), —CN, C1-C10-alkyl, C3-C8-cycloalkyl, C2-C10-alkenyl, C2-C10-alkynyl, -$OR^7$, —$NO_2$, —$CF_3$, —$S(O)_rR^8$, —$NR^6R^7$, —$COR^7$, —$CO_2R^7$, —$CONR^6R^7$;

X is a peptide of 1–20 amino acids;

$R^2$ is a) C1-C10-alkyl, b) C2-C10-alkyl-Y, c) —$(CH_2)_n$-aryl, wherein aryl is as defined above;

Y is a) —$NHC(NH)NH_2$, b) —$NH_2$, c) —$SC(NH)NH_2$, d) —$OR^9$, e) —$SR^9$;

$R^5$ and $R^6$ are independently a) H, b) C1-C8-alkyl, c) C1-C8-alkoxy, d) C3-C8-cycloalkyl, e) —$CO_2R^7$, f) —$(CH_2)_m$-phenyl;

$R^7$ is
 a) H,
 b) phenyl,
 c) benzyl,
 d) C1-C8-alkyl;
$R^8$ is
 a) phenyl,
 b) C1-C4-alkyl,
 c) C1-C4-alkoxy,
 d) —$CF_3$;
$R^9$ is
 a) H,
 b) C1-C2-alkyl,
 c) phenyl or phenyl optionally substituted with a substituent selected from the group consisting of halo (F, Cl, Br, I), —CN, C1-C10-alkyl, C3-C8-cycloalkyl, C2-C10-alkenyl, C2-C10-alkynyl, —$OR^7$, —$NO_2$, —$CF_3$, —$S(O)_rR^8$, —$NR^6R^7$, —$COR^7$, —$COR^7$, —$CO_2R^7$, —$CONR^6R^7$;
n is 0 or 1;
m is 0 to 2;
r is 0 to 2;
comprising suspending a compound of the formula

$$R^1\text{-}X_n\text{—NHCH }(R^2)\text{—}BR^3R^4 \qquad (I)$$

wherein $R^1$, $R^2$, X, Y, $R^5$, $R^6$, $R^7$, $R^8$, $R^9$, n, m and r are as defined above; and
$R^3$ and $R^4$ are
 a) C1-C8-alkoxy, or
 b) when taken together $R^3$ and $R^4$ form a cyclic boronic ester where said chain or ring contains from 2 to 20 carbon atoms and, optionally, a heteroatom selected from the group consisting of N, S, or O,
in a mixture of water and a water-immiscible organic solvent in which said compound of formula (II) is less soluble than in water, said mixture containing an organic boronic acid acceptor which is more soluble in the water-immiscible organic solvent than in water and is selected from the group consisting of phenyl boronic acid, butyl boronic acid, pentyl boronic acid, hexyl boronic acid or cyclohexyl boronic acid, said organic boronic acid acceptor being present in a amount equal to at least 1 equivalent of said compound of formula (I), wherein the amount of water present in said mixture is sufficient to completely dissolve the compound of formula (II) formed and the amount of water-immiscible organic solvent present in said mixture is sufficient to completely dissolve said organic boronic acid acceptor and the boronic ester reaction product formed; stirring the resulting reaction mixture for approximately one hour before allowing the reaction mixture to separate into two distinct phases; separating the phases; and recovering the compound of formula (II) from the separated aqueous phase.

2. The method of claim 1 wherein the water-immiscible organic solvent is selected from the group consisting of diethyl ether, carbonteterachloride, chloroform, methylene chloride, ethyl acetate, benzene, toluene or hexane.

3. The method of claim 2 wherein the organic boronic acid acceptor is phenyl boronic acid.

4. The method of anyone of claims 1 to 3 wherein the amount of organic boronic acid receptor present in the suspending step is in the range of 3 to 5 molar equivalents of the amount of the compound of formula (I) present in said step.

5. The method of claim 1 wherein the compound of formula (II) is recovered from the seperated aqueous phase by the evaporation of water from said phase.

6. The method of claim 5 wherein the evaporation of water is by means of a rotary evaporator.

7. The method of any one claim from claim 1 to claim 6, wherein the compound of formula II is H-(D,L)boroVal-OH.trifluoroacetyl acid and the compound of formula I is H-(D,L)bor Val $C_6H_{12}$.trifluoroacetyl acid.

8. The method of any one claim from claim 1 to claim 6, wherein the compound of formula II is hydrocinnamoyl-Pro-boroLys-OH benzene sulfonic acid and the compound of formula I is hydrocinnamoyl-Pro-boroLys-$C_{10}H_{16}$ benzene sulfonic acid.

* * * * *